US006180070B1

United States Patent
Benson

(10) Patent No.: US 6,180,070 B1
(45) Date of Patent: Jan. 30, 2001

(54) INFECTIOUS WASTE TREATMENT SYSTEM

(75) Inventor: W. Lynn Benson, Salt Lake City, UT (US)

(73) Assignee: Lofta Hammer Holdings LTD, Las Vegas, NV (US)

( * ) Notice: Under 35 U.S.C. 154(b), the term of this patent shall be extended for 0 days.

(21) Appl. No.: 09/110,220

(22) Filed: Jul. 6, 1998

(51) Int. Cl.$^7$ ........................................... A61L 2/00
(52) U.S. Cl. .................... 422/295; 241/27; 241/38; 241/43; 241/154; 241/606; 422/37; 422/297; 422/308; 422/309
(58) Field of Search ................ 422/37, 295, 297, 422/308, 309; 241/27, 38, 43, 606, 154

(56) References Cited

U.S. PATENT DOCUMENTS

| | | | |
|---|---|---|---|
| 4,578,185 | * | 3/1986 | Wilson et al. . |
| 5,119,994 | * | 6/1992 | Placzek ............................. 422/26 X |
| 5,209,411 | * | 5/1993 | Dineley et al. . |
| 5,213,774 | * | 5/1993 | Noetzel ............................ 422/309 X |
| 5,387,350 | * | 2/1995 | Mason ................................ 422/32 X |
| 5,520,888 | * | 5/1996 | Berndt ............................... 422/28 X |
| 5,720,438 | * | 2/1998 | Devine et al. ..................... 422/27 X |
| 5,820,044 | * | 10/1998 | Greco .................................. 241/154 |

* cited by examiner

Primary Examiner—Krisanne Thornton
(74) Attorney, Agent, or Firm—Thorpe, North & Western, LLP

(57) ABSTRACT

An system for treatment of infectious waste including a impactor coupled to a mixing drum that can be pressurized, infectious waste and a treatment fluid comprising a substance effective in killing pathogenic organisms being introduced directly into the impactor where the waste is pulverized forming unrecognizable particulate matter mixed with fluid, and the waste from there being introduced into the drum for mixing and subsequently pressure treatment by providing a superatmospheric pressure in the drum to drive chemicals effective in killing pathogenic organisms into voids in the solids and also into spore walls and cell membranes to provide a more speedy and effective kill.

21 Claims, 8 Drawing Sheets

INFECTIOUS WASTE TREATMENT SYSTEM

SPECIFICATION

BACKGROUND OF THE INVENTION

1. Field of the Invention

This invention relates generally to methods and apparatus for reducing or eliminating hazards inherent in disposal of infectious waste. More particularly, the invention relates to a system which physically alters the infectious waste to reduce it to particulate matter and kills pathogens in the waste so that it can be safely disposed of in a conventional manner, for example in a sanitary landfill.

2. Description of Related Art

In disposal of infectious waste, specifically waste produced incidental to medical research, testing, and treatment for example, it is recognized that hazards are inherent in handling and disposition of such waste. This is due for example to the physical nature of the waste, which may include sharps which may cause injury and ready transmittal of pathogens due to accidental wounds; and also due for example to the amount and nature of pathogenic material which may be contained in the waste, and transmitted by contact or by airborne transmission to persons exposed to the waste without due precautions being taken. The hazard may persist as long as conditions conducive to continued existence of the pathogens persist. Accordingly, disposal by customary means into a sanitary sewer, and/or into a sanitary landfill may pose immediate and long-term health risks. Consequently methods and apparatus for rendering medical waste less hazardous have been developed, and new methods which more effectively mitigate the above-mentioned hazards are the subject of intense interest by persons concerned with disposal of such waste and the protection of public health and the physical environment.

Systems for disposal of medical waste have heretofore generally involved a number of treatment steps, each step requiring apparatus to effect the step. For example, a presently known treatment apparatus can include: a shredder for opening vials and other assorted containers and bags; a system for applying disinfectant, usually involving a sump and recirculation system to collect excess disinfectant, which may be mixed with waste fluids; a means to render excess fluid safe for disposal and transfer to a sanitary sewer; a hammermill or other means to pulverize solid waste, a pressure vessel wherein waste and disinfectant are subjected to a superatmospheric pressure to improve disinfectant penetration into voids; and a separator to separate solids from fluids and excess disinfectant, and means to transport waste to and from all the aforesaid during the treatment process. As can be appreciated, such an apparatus is usually large, and also relatively costly due to the number of treatment steps which must be provided for. Such an apparatus takes considerable space and may be uneconomical for smaller medical facilities to acquire and operate.

Furthermore, known infectious waste treatment systems generally have a limited capacity, for example in the range of eight hundred to twelve hundred pounds per hour. This is in spite of their relatively large size. This is due to time required to separate fluids from solids in known systems for example. A system which more speedily neutralizes hazards attendant handling and disposal of the waste will reduce the trouble and cost involved and encourage proper disposal of waste. For example, a smaller system would be advantageous in terms of both cost and space required, if adequate capacity can be maintained. Likewise operator time required can be reduced if waste is processed faster.

Moreover, it has been recognized that a system which is simplified in comparison with known systems would give further advantages over known systems in terms of both initial cost and operational cost over the life of the system. For example known systems with numerous treatment steps and components to carry them out are susceptible to a like number of equipment failures. This can cause difficulty beyond the system itself, as a backlog of infectious waste building up due to a disposal equipment problem can disrupt day-to-day operation of a facility producing such waste.

Another problematic aspect of some known systems is that periodically disinfectant must be dumped and fresh disinfectant supplied. As mentioned, disinfectant may be mixed with fluids from the waste. As will be recognized by those skilled in the art elimination of the need to periodically dump and refresh the disinfectant would avoid the further complication of the treatment process it represents.

Elimination of the need for access to a sanitary sewer line has also been recognized as a desirable objective, as this will reduce costs in many installations. Further, introduction of a powerful disinfectant chemical may have a deleterious effect on desirable biological processes in treatment of effluent from the sanitary collection system where the disinfectant is introduced.

What is needed, and has heretofore not been available, is a system that mitigates these problems. The present invention is directed to fulfilling this need.

SUMMARY OF THE INVENTION

Briefly, and in general terms, the present invention accordingly provides in combination an impactor adapted to pulverize the infectious waste by impact and an injector adapted to inject treatment fluid into the infectious waste and a mixer adapted to mix pulverized waste with treatment fluid. The system also includes a pressurizable drum having an interior configured to hold pulverized waste and treatment fluid at a superatmospheric pressure and an air pump adapted to apply a surcharge of air to the pressurizable drum to create a condition of superatmospheric pressure within the pressurizable drum, whereby improved absorption of treatment fluid by the pulverized waste and pathogenic organisms contained therein is enabled.

In a more detailed aspect the mixer can comprise said pressurizable drum, so that pressurization can be performed in the same container as mixing. In this instance waste is fed into the impactor where it is pulverized, treatment fluid is added, which treatment fluid comprises a substance which kills pathogenic organisms, and the mixture is transferred into the mixing drum. The waste and treatment fluid are mixed, then subjected to pressure, and then discharged from the mixer. The treated waste is moist and pulverized to a point where the waste is unrecognizable. The pathogenic organisms in the treated waste being killed, the waste can then be disposed of as ordinary waste.

These and other aspects and advantages of the invention will become apparent from the following detailed description, and the accompanying drawing figures, which illustrate by way of example the features of the invention.

DESCRIPTION OF THE PREFERRED EMBODIMENTS

Figure 1:
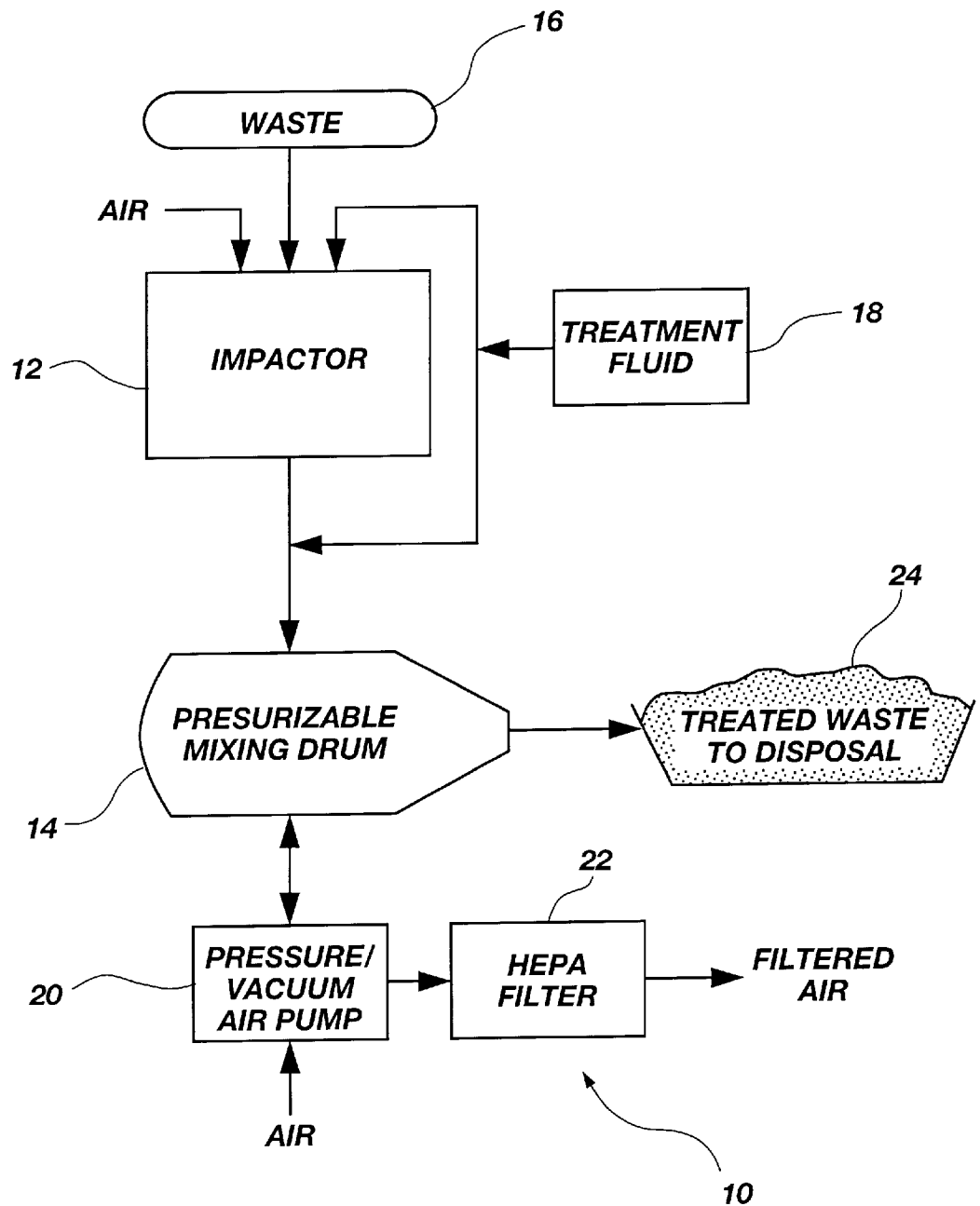
FIG. 1 of the drawings is a schematic representation of an illustrative embodiment of the system for treatment of infectious waste according to the invention.

As shown schematically in FIG. 1 for purposes of illustration, the system for treatment of infectious waste 10 of the invention includes an impactor 12 and a pressurizable mixing drum 14. Waste 16 is fed into the impactor, and treatment fluid, which in one embodiment is a solution of Sodium Hypochlorite (NaOCL) in water having a concentration of 3000 ppm, is supplied from a source of treatment fluid 18. Air is also drawn into the impactor when waste is being added, reducing the escape of airborne pathogens from the system, by reason of an air pump 20 which by selective valving can be made to draw air through the system to be expelled through a filter 22, for example a HEPA filter, which filters out pathogenic organisms. The system according to the invention is simpler than present systems accomplishing the same task, and does not require a sewer drain connection for dumping used treatment fluid for example, as the treatment fluid is more effectively used and exits mixed with the waste as will be described below.

The treated waste 24 is pulverized waste mixed with treatment fluid, and ideally is damp, as all solid waste particulate and fibrous matter is wetted, but not so wet as to cause excess treatment fluid to be present and leach out of the treated waste. The treated waste can be disposed of as ordinary waste in a conventional matter, the volume having been reduced by as much as approximately 90 percent and the waste having been rendered safe by killing essentially all pathogenic organisms within the limits of detection.

Figure 2:
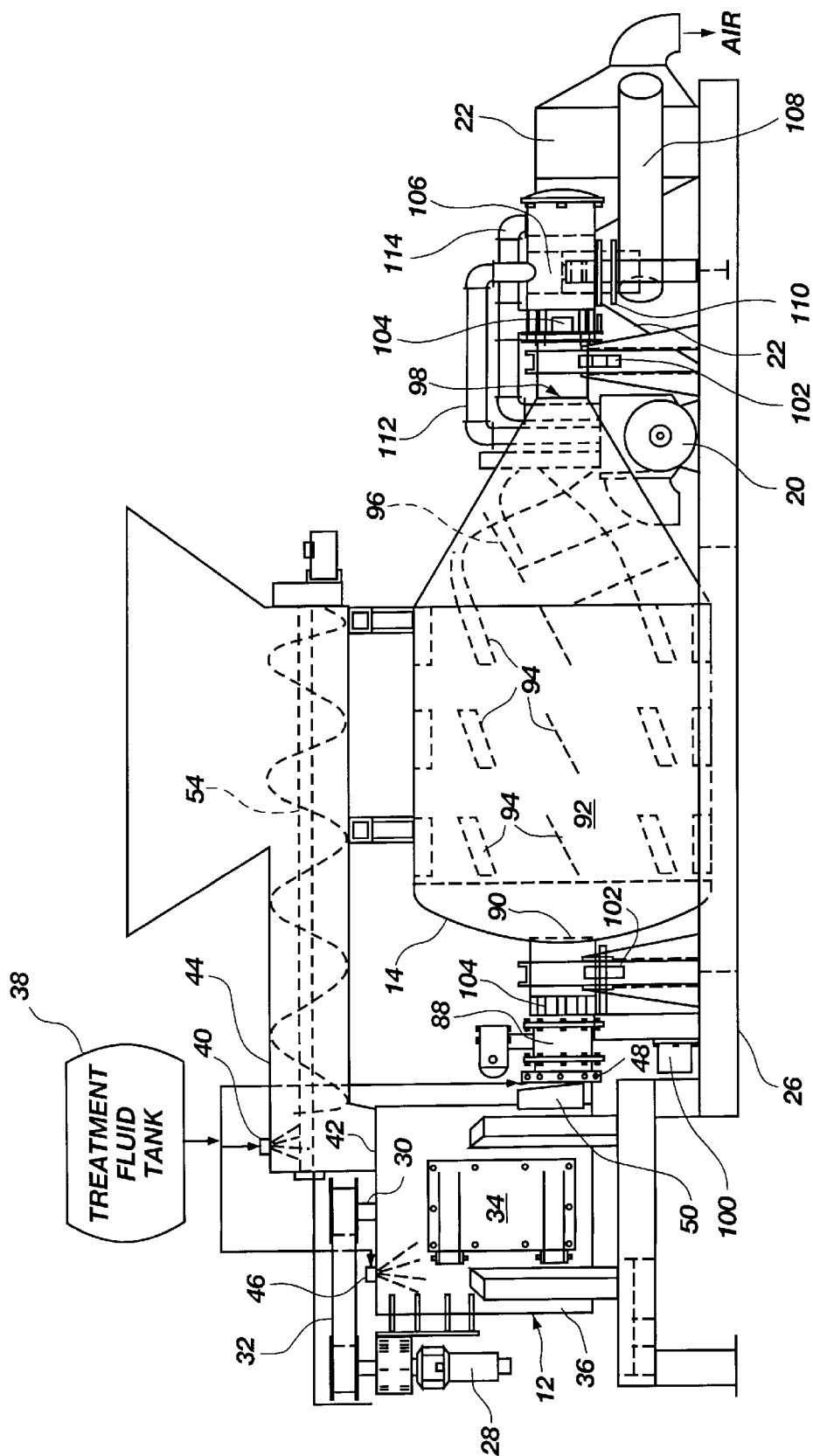
FIG. 2 of the drawings is a side elevation view of an illustrative embodiment of the system shown in FIG. 1.
Figure 3:
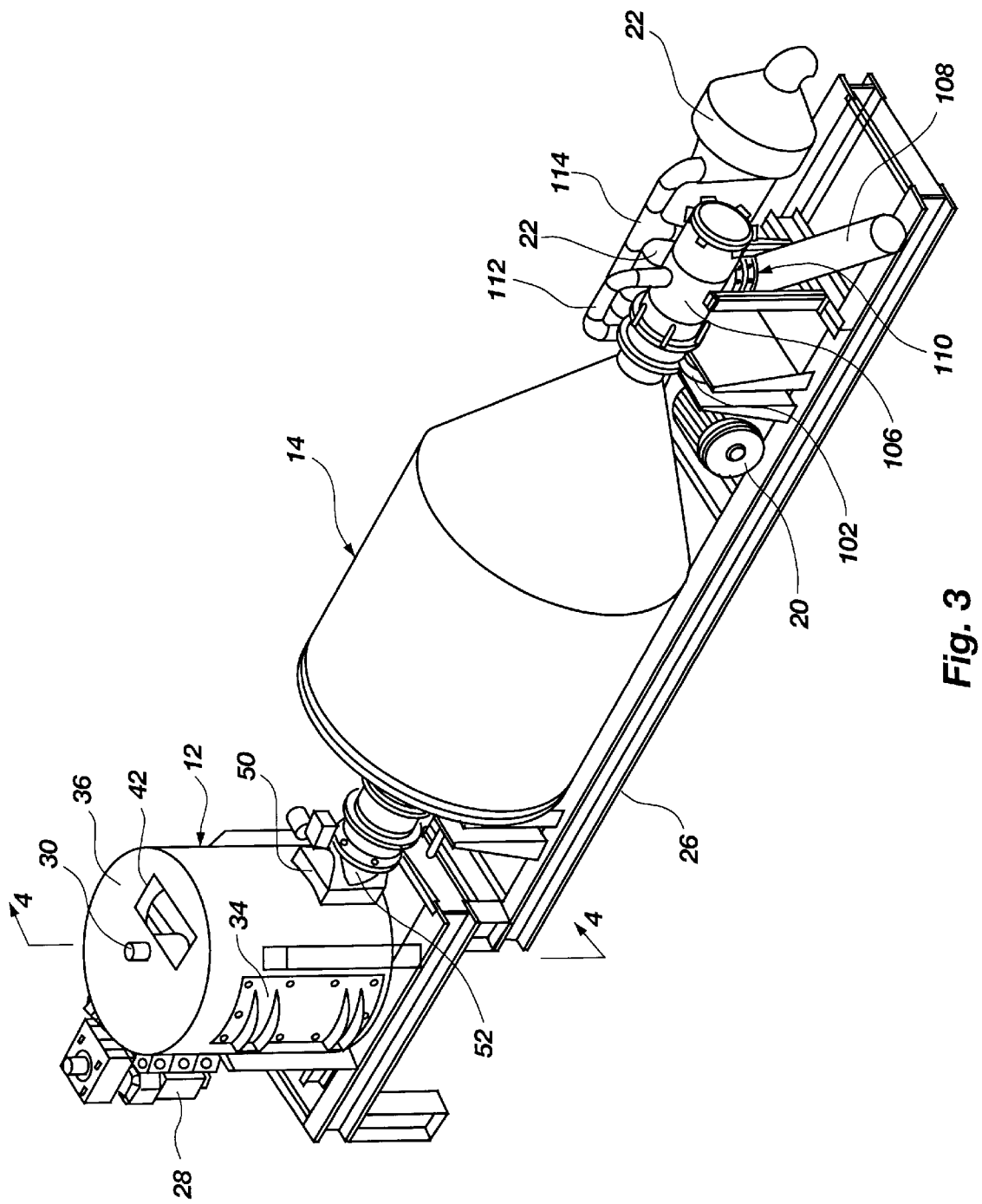
FIG. 3 of the drawings is a perspective view representation of the system shown in FIG. 2.

With reference to FIGS. 2 and 3, in one embodiment the invention is embodied in a system for treatment of infectious waste including an impactor 12 and a rotatable and pressurizable mixing drum 14 carried by a frame 26. The impactor is powered by an electric motor drive 28 connected to a rotor shaft 30 by a belt 32. The motor drive turns the shaft at a speed of approximately 1400 to 1600 rotations per minute. The motor drive in another embodiment could be a hydraulic unit. An access door 34 is provided in a housing 36 welded to the frame. A second access door (not shown) is located on an opposite side of the impactor.

A treatment fluid tank 38 is shown schematically, and can comprise in one embodiment a drum which is replaced or replenished as fluid is depleted. In another embodiment (not shown) water and NaOCL tanks are separately provided and the fluids are mixed in proportion as required before the treatment fluid is injected into the system. With reference to FIGS. 2 and 3 as shown, the treatment fluid is injected through injectors at one or more locations comprising the location of a first injector 40 above an inlet 42 defined by the impactor housing. The first injector is mounted in a hopper head 44 wherethrough waste is fed into the impactor 12. A second injector 46 is located on the impactor, disposed in the impactor housing 36 so as to inject treatment fluid directly into the impactor. A third injector 48 is located at a location adjacent an outlet 50 of the impactor where multiple injectors 48 are located around the circumference of a conduit 52 for carrying waste from the impactor 12 to the pressurizable mixing drum 14. This can be further appreciated with reference to FIG. 7A which shows a similar arrangement used in another embodiment.

Returning to FIGS. 3 and 4, waste is fed into the system through the hopper head 44, which in the illustrated embodiment includes a screw conveyor 54 for feeding the waste at a selected rate. A cart dumper (not shown) could also be provided which would allow waste, conventionally contained and carried in red bags, to be fed without handling the bags. A hydraulic ram arrangement can be substituted for the screw conveyer to controllably feed waste into the impactor. The hopper head prevents waste that may be thrown back out from the impactor inlet 42 from escaping, and acts to direct waste into the impactor. The hopper head also provides a chamber immediately above the impactor inlet where treatment fluid is first injected into the waste stream.

Waste enters the impactor where it is pulverized so that solid waste components are unrecognizable. Needles and other sharps are pulverized into particulate matter, and accordingly rendered much less hazardous. Plastic parts are broken up, cracked and their surfaces roughened and fiberized to some extent. Glass is particlized, wovens are fiberized, and plastic films and containers, tubing, and the like are reduced to a confetti-like state, also with roughened surfaces. This greatly increases the surface area of the waste and allows treatment fluid to be absorbed into and adhere to the surfaces of the solids components of the waste. Accordingly chemicals which are adapted to kill pathogens are retained in the waste, even after treatment. An advantage of the system is that waste is introduced directly into the impactor, and accordingly jamming, and the possibility that waste will not be pulverized, are greatly reduced. This is in contrast to known systems having shredders or flail mills as a first step in treatment, which are susceptible to jamming or incomplete pulverization which may cause a jam there or elsewhere beyond the first step but before pulverization. This results in a safer system in that workers are not required to enter the system to clear a shredder jam or the like for example.

Moreover, in contrast to prior systems, which incorporate flail mills and/or hammer mills with screens which effect a size reduction primarily by a shearing action, the impactor of the present invention effects size reduction by impact primarily. Where shearing-type machines give an end product where the particulates produced have relatively cleaner surfaces, the use of an impactor gives heretofore unrealized advantages in that the surfaces of the particulates are relatively more rough, and for the reasons set forth above the solids resulting have an increased capacity to retain fluids. Accordingly fluids in the waste, as well as treatment fluid can be retained in the treated waste and do not need to be separately disposed of. As can be appreciated, wastes having a very high ratio of liquids in comparison with solids may need to be combined with wastes having a relatively high ratio of solids as compared with liquids so as to produce an end-product treated waste stream where liquids are retained. This size reduction is accomplished in a very short time, for example approximately 5 seconds is a typical time for waste to pass through the impactor.

Figure 4:
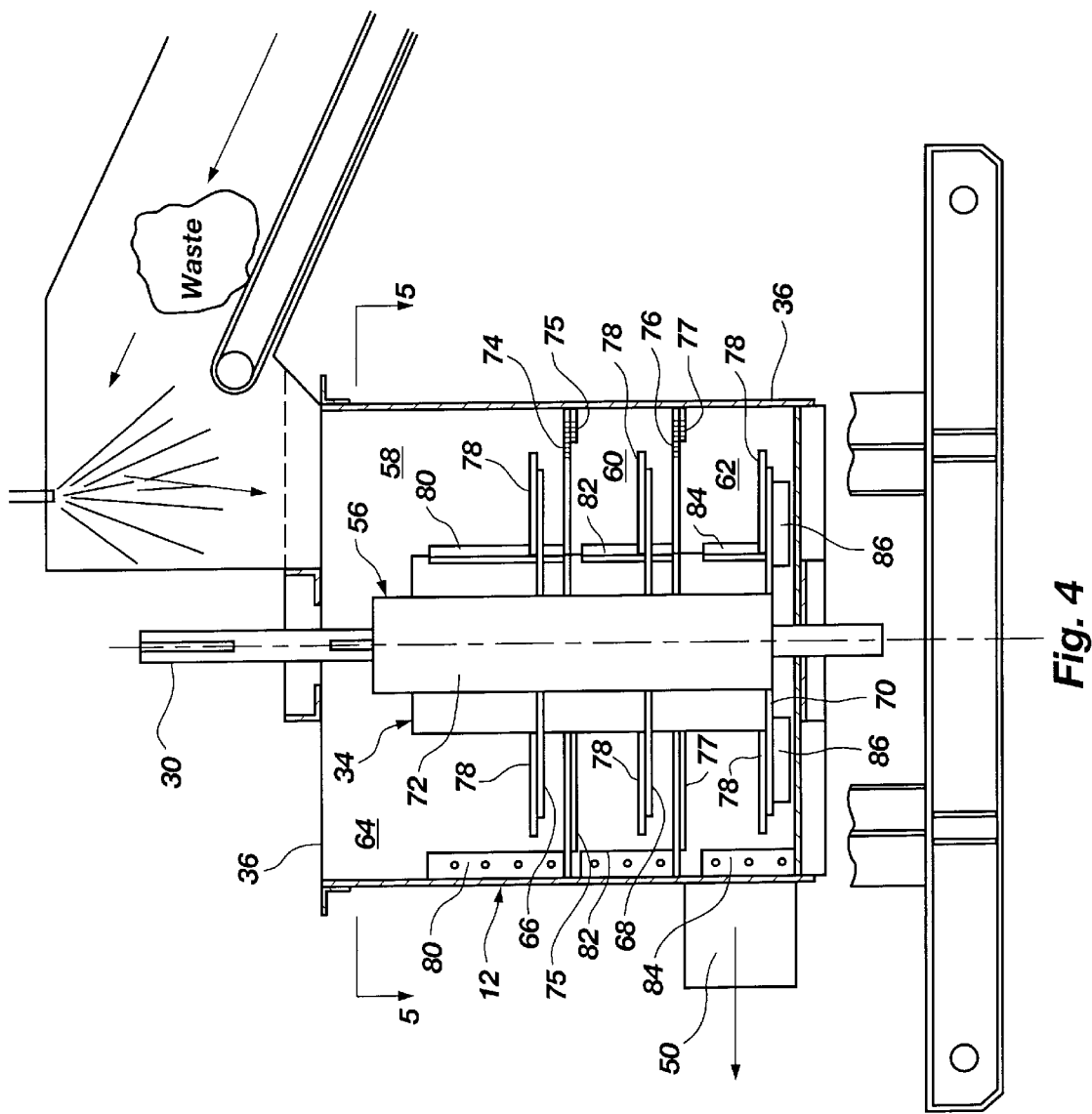
FIG. 4 of the drawings is a side elevation view, partially in section taken along line 4—4 in FIG. 3, of an impactor according to the invention, showing further interior details.
Figure 5:
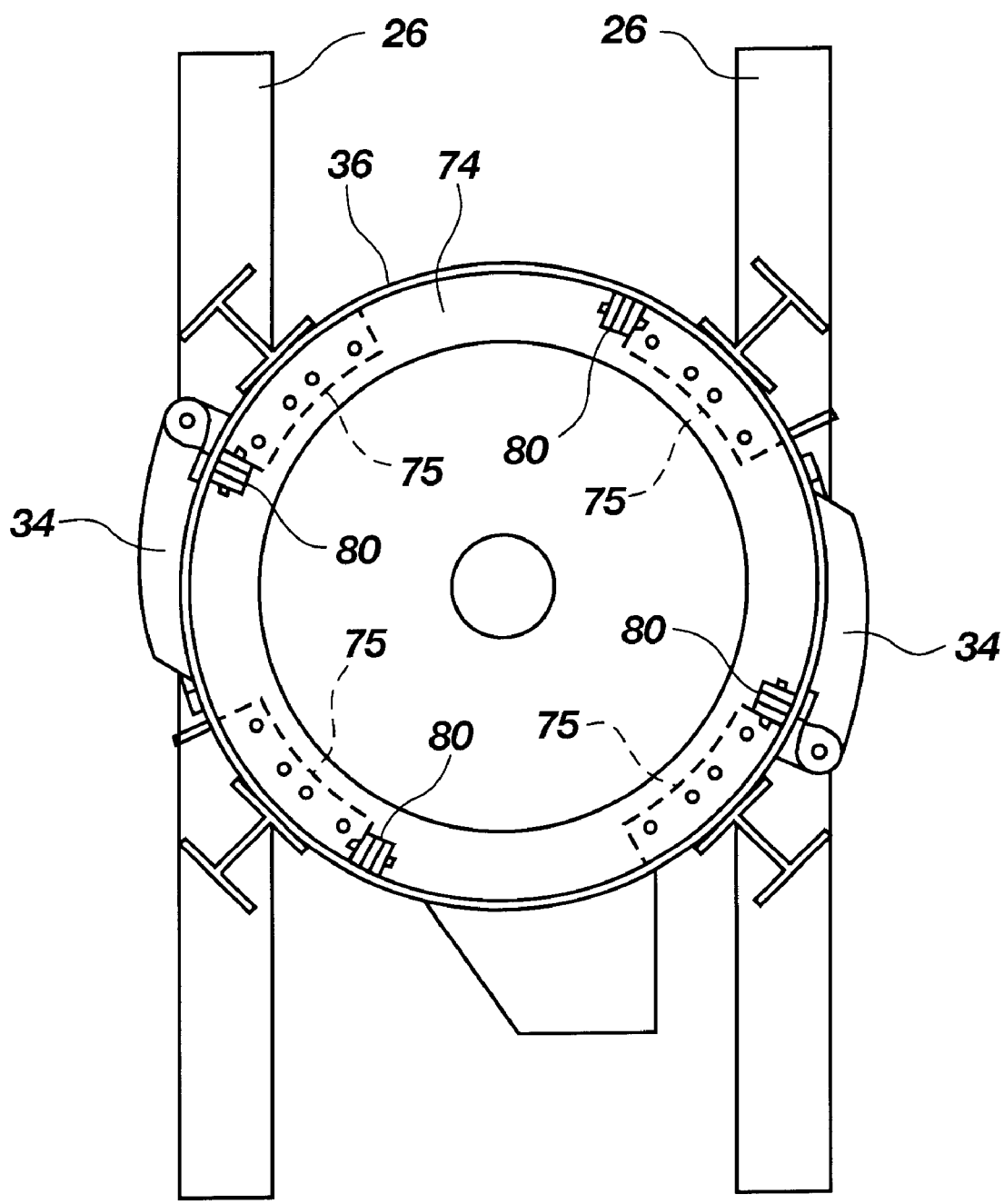
FIG. 5 of the drawings is a plan view, partially in section taken along line 5—5 in FIG. 4, of the impactor shown in FIG. 4.

With reference to FIGS. 4 and 5, further details of the impactor 12 can be appreciated. The impactor comprises a rotor 56 carried by the rotor shaft 30 in turn supported by bearings (not shown) carried by the impactor housing 36. The impactor has three stages, comprising chambers 58, 60, 62 defined within and collectively comprising an interior chamber 64 of the impactor. The stages are defined by horizontal plates 66, 68, and 70 welded to a central hub 72 of the rotor, and horizontal shelves 74 and 76, supported by and bolted to flanges 75 and 77. The flanges are in turn welded to and supported by the housing 36. The first shelf 74 separates the first and second stages, and the second shelf 76 separates the second and third stages. Shelves 74 and 76 extend into the interior chamber so as to underlie impact elements 78 carried by the horizontal plates of the rotor, but not so far as to prevent installation and removal of the rotor, at least a small clearance between the shelves and the horizontal plates being provided for this purpose.

In an alternate embodiment, each of the shelves 74, 76 are comprised of four segments bolted to the flanges 75, 77 at their ends. This configuration allows the shelves to be installed after the rotor 56 is in place. In this embodiment wider shelves can be used, as a clearance between the horizontal plates 66, 68 and 70 of the rotor and the shelves need not be maintained for constructability. Generally, wider shelves give rise to longer retention time in the impactor and this is one design factor that can be varied during the operational life of the impactor to control the amount of time the waste material 16 is processed in this embodiment. Using a rotor of different configuration with regard to placement of the horizontal plates 66, 68 and 70 along the hub 72 with respect to the shelves can also vary the retention time. As can be appreciated care must be taken with regard to spacing between elements so that the impactor is not susceptible to jamming.

The first stage, comprising the first chamber 58, is large enough to accommodate even large bags and sharps containers, so that all waste anticipated may be fed directly into the impactor. For example in one embodiment the impactor is approximately 56 inches in diameter, and the distance between an upper part of the housing 36 and the impact elements 78 carried by the first horizontal plate 66 is approximately 24 inches. The size of the second and third stage can be, and is, smaller in the illustrated embodiment because waste is reduced in size in the first stage at least to the point where it can pass between the first shelf 74 and the first horizontal plate 66 into the second chamber 60 comprising the second stage. In the second stage waste is further reduced in size. Waste solids particulate matter then is subsequently again reduced in size in the third chamber 62 before passing out of the impactor through the outlet 50 defined by the housing 36 and into the conduit 52 connecting the impactor outlet to the pressurizable mixing drum 14.

At each stage size reduction by impact is accomplished by impact of solids with the rotating impact elements 78, and also by impact with target plates 80, 82, and 84 disposed around the periphery of the interior chamber 64 in each of the three stages, respectively. In the illustrated embodiment four target plates per stage are provided and six impact elements 78 per horizontal plate (66, 68, 70) are provided, arranged symmetrically for rotor balance. As can be appreciated, impact of the solids with the impact elements 78 imparts force to the solid components of the waste, and the solids are thrown against the housing 36 and target plates 80, 82, 84 where further size reduction takes place by impact. This process is repeated until a particular particle's trajectory takes it between the horizontal plate 66, 68 and the shelf 74, 76 of the first and second stages respectively, or out through the outlet of the impactor from the third stage.

The impact elements 78 and target plates 80, 82, and 84 of the first, second and third stages, respectively, are susceptible particularly to wear, and for this reason they can comprise separate replaceable elements. In one embodiment the impact elements 78 are removed and reinstalled backwards with respect to how they are initially installed midway through their service life, which is of course almost twice as long as it could otherwise be due to the fact that a new impact surface, located on a leading side of the element as it rotates is provided. In another embodiment the direction of rotation is reversed approximately one half of the way through the service life of the impact elements to provide even wear on both sides. In one embodiment the target plates are provided with removable plate elements on one or both sides which can be replaced when they become excessively worn. Access doors 34 are provided on each side of the impactor for maintenance access, for example for inspection and/or replacement of the impact elements 78 and target plates 80, 82, 84. As can be appreciated a tight seal is provided around this door to prevent escape of particulate matter or aerosols of waste and treatment fluids.

Impeller flanges 86 are welded to a bottom surface of the third and lowest horizontal plate 70 of the rotor 72. These sweep the bottom of the impactor and impel air, fluids, and particulate matter outwardly, driving them through the outlet 50 of the impactor. This action, in combination with that of the impact elements 78 carried by the rotor moves air through the impactor, providing additional impetus for the drawing of atmospheric air into the impactor from the hopper head 44. This action in combination with that of the air pump 20 which pulls air through the system and through HEPA filters, mitigates the effects of pulverized matter and aerosols being ejected from the impactor, as such substances are drawn back into the impactor with the air current before they can escape the hopper head 44.

The three stage impactor 12 provides a uniform effluent stream of pulverized waste solid constituents and aerosol waste liquids and treatment fluids. Treatment fluid introduced into the waste 16 fed into the impactor is driven into voids created in the solids under great force occasioned by and in connection with numerous impacts. No screens or the like, which may jam or clog, are used in the impactor. The number of particles exceeding a selected size, for example ½ inch maximum diameter in one embodiment, in the waste exiting the impactor is insignificant low. This is the result of repeated impacts to the solids through all three stages. Accordingly, maintenance of screens and the like attendant former use of conventional hammer mills and the like dependent on such screens or grates to insure a particulate size below a certain value is eliminated.

As indicated above, the spacing between the horizontal plates 66, 68, 70 of the rotor 56 and the shelves 74, 76 and floor of the impactor housing 36 controls dwell time of the waste 16 in the various stages. This in turn affects particle size of the solids components of treated waste. As a result of enlarging or decreasing the spacing, larger or smaller particles, respectively, will be derived.

Depending on the nature of the waste to be processed, or the volume of waste to be processed, the impactor can be scaled up or down in size. For example in the illustrated embodiment the impactor is approximately 54 inches high and approximately 54 inches in diameter. The inlet is approximately 20 inches by 24 inches and the outlet is approximately 12 to 16 inches in diameter. Scaled-down units of 36 inches height and diameter can be used at a small lab or hospital, for example, and units of 72 inches height and diameter can be used in high capacity applications associated with a large facility or central processing installation for example.

Moreover, while a three-stage design is shown, fewer stages, or more stages, could be employed. For example waste having a high liquid content or having highly frangible constituents such as glass would require fewer stages, provided that the spacing or clearance between plates 66, 68, 70 and shelves 74, 76, 78, and other features were designed to provide sufficient retention time in the impactor that all waste solids are reduced to the desired size in the one or two stages provided. Wovens, paper, and the like, generally require more stages if other factors and considerations in the design are held the same.

Advantages achieved by use of the impactor, as opposed to other types of shredding machinery generally used in prior systems is that the amount of chemical treatment fluid required to treat the waste is reduced. This apparatus gives the particle texture described above, and fiberizes the non-slick wovens, non wovens, paper and the like, and ends and edges of solids are generally more frayed, porous, and absorbing, therefore less chemical is required to penetrate and permeate the treated waste. On the other hand it also increases the capacity to absorb fluid in the treated solids, and so liquid wastes mixed with treatment fluid can be more effectively retained, eliminating the need for separate liquid disposal as mentioned above.

Returning now to FIGS. 2 and 3, the pulverized waste is ejected from the impactor 12 through a knife valve 88 and through an inlet 90 at a first end 91 of the drum 14 into a mixing chamber 92 within the pressurizable mixing drum, having further treatment fluid injected as it exits the impactor as before described. In the mixing chamber essentially complete contact of treatment fluid comprising the killing agent NaOCL with the solids is assured by mixing of the impactor effluent waste stream and the treatment fluid by rotation of the drum. In one embodiment approximately 1.5 liters of treatment fluid per cubic foot of waste is mixed in, assuming a typical mix of infectious waste. The optimal amount of fluid used per volume or unit of mass of a particular type of waste or mix of waste types typical at a particular facility is determined by testing the treated waste product produced in several batches produced at various levels of treatment fluid added per unit of waste. Thereafter the operator can add treatment fluid as necessary for a particular batch of waste to be processed, based on the results of the earlier determination of the optimal amount of such fluid per unit measure of waste.

As before described, a small amount of this treatment fluid is added before and/or during treatment in the impactor 12. This may be for example approximately 5 percent of the total mix by weight. The rest of the treatment fluid is added as the waste leaves the impactor. A metering system (not shown) including a flow meter of conventional design and relative sizing of spray orifices of the respective injectors 40, 46, 48 can be employed to inject the proper amount of treatment fluid into the waste stream passing through the inlet 42 and the conduit 50 between the impactor 12 and the pressurizable mixing drum 14.

Mixing flights comprising flanges 94 disposed to provide a spiraling mixing action as the drum 14 is rotated in a first direction are provided. By reversal of the direction of rotation of the drum to a second direction the mixing flights and further spiral flanges 96 carry the treated waste out of the pressurizable mixing drum 14 through an outlet 98.

The pressurizable mixing drum 14 is formed of stainless steel. Rotation of the drum is effected by a drum motor drive 100 turning rollers 102 rotatably supporting the drum. In another embodiment (not shown) a chain and sprocket arrangement driven by a hydraulic or electric motor can be provided. In the illustrated embodiment serpentine seals 104 are provided at each end of the drum so that a sealed and pressurized environment can be created in the interior mixing chamber 92 of the drum 14. The drum is connected to a effluent conduit 106 connected to a treated waste screw conveyor tube 108 through a second knife valve 110 disposed below, and connected at a right angle to, the effluent conduit 106. The knife valve allows the conduit and drum to be sealed and isolated from the atmosphere at the outlet 98 by closing the valve.

In operation of the system 10 the second knife valve is closed as waste is fed into the system. Air is drawn into the system by the air pump 20 trough an air conduit 112 connected to the effluent conduit 106. As can be appreciated this draws air through both the drum 14 and the impactor 12. Air is exhausted from the pump 20 through the HEPA filters 22 mounted on the frame 26 adjacent to the effluent conduit 106 via an air exhaust conduit 114. After a batch of pulverized waste and treatment fluid is processed through to the pressurizable mixing drum 14 which is rotating in the first direction causing mixing, mixing is stopped and the first knife valve 88 is closed. Air flow from the air pump 20 is reversed drawing air from the atmosphere to provide a surcharge in the pressurizable mixing drum. This surcharge is approximately 10 psi above atmospheric pressure. The excess pressure tends to drive treatment fluid deeper into voids in solids, and on a microbic level through cell membranes and spore walls for example, to kill pathogenic organisms more effectively. Pressurization decreases the time required for kill of the pathogenic organisms in the waste. Dwell time in the pressurized mixing drum is approximately 5 minutes in one embodiment, and may be somewhat less in another embodiment. Pressurization also reduces the amount of chemical required for kill as the chemical used is used more effectively.

After mixing and pressurization, the air pump 20 is turned off and the pressure is released through the HEPA filters 22. The second knife valve 110 is opened after the pressure is released. The direction of rotation of the pressurizable mixing drum 16 is reversed and treated waste is moved out of the drum by action of the mixing flights and spiral flanges 96 as the drum rotates. Waste falls through the knife valve into the screw conveyer 108 and is transferred to a collection means (not shown) for eventual disposal as ordinary waste, for example by placement in a sanitary landfill. The illustrated embodiment is capable of a processing rate in excess of 3000 pounds of infectious waste per hour. This is a great deal faster than previous systems, particularly those of the same size or the same cost.

As can be appreciated by those skilled in the art, the screw conveyor 108 at the effluent conduit 106, as well as the screw conveyor 54 in the hopper head can be replaced by a conveyor belt or other means of moving waste. Likewise other variations contemplated include but are not limited to: providing a plurality of pressurizable mixing drums selectively connectable to the impactor so that capacity can be increased; using hydraulic motors instead of electric motors to drive components such as belt or screw conveyors, the air pump, the mixing drum, as well as the impactor; automation of the system by providing actuators (electrical or hydraulic) to actuate the knife valves 88, 110, and manual or automatic control of the various motor drives, air pump and treatment fluid pump (not shown) from a single control location on the apparatus.

Figure 6:
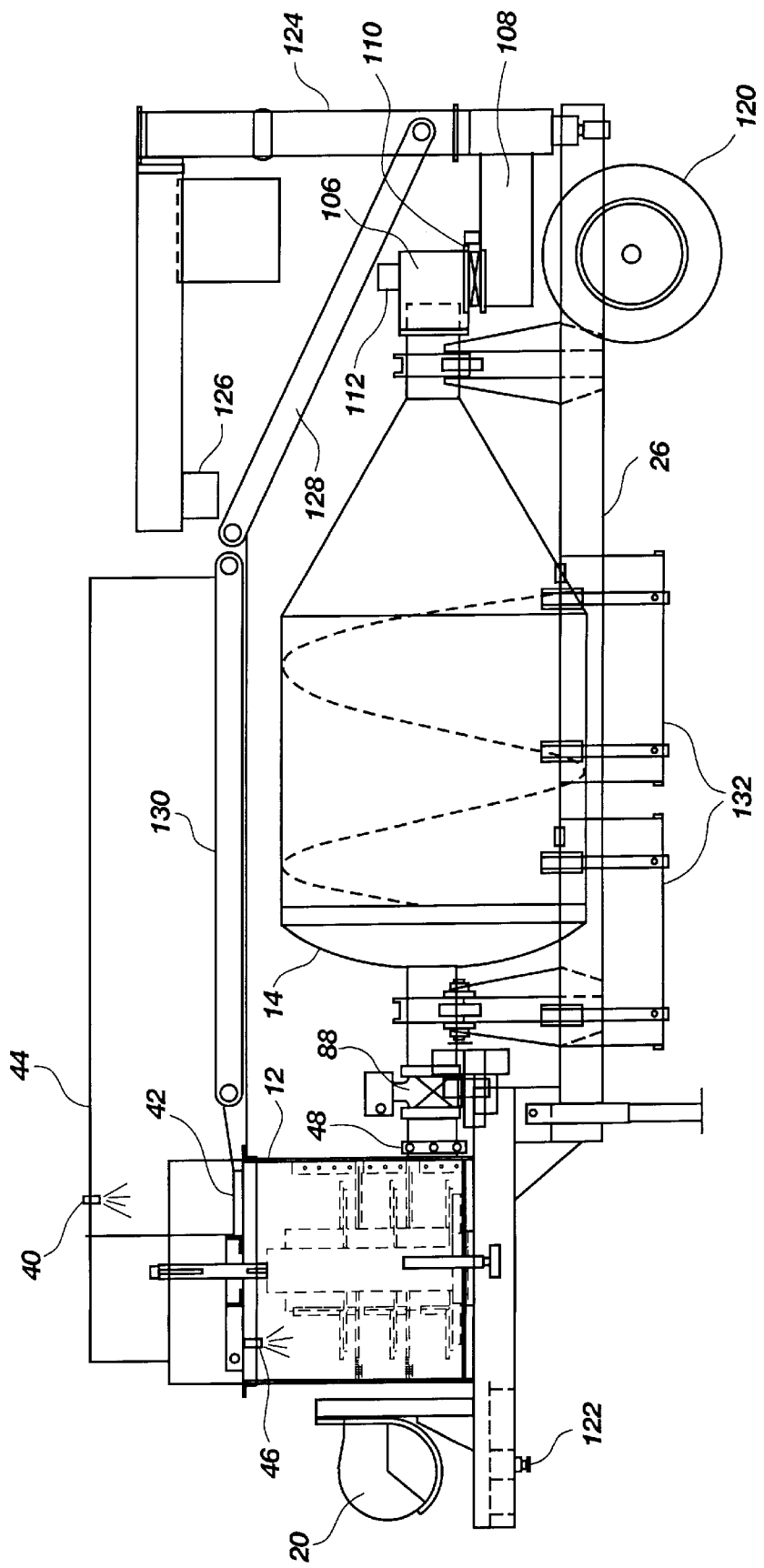
FIG. 6 of the drawings is a side elevation view of an embodiment of the invention where the system is configured to be mobile.

Another variation is to make the system mobile. This is illustrated in the embodiment shown in FIG. 6. The mobile system operates essentially as described above, accordingly only certain differences will be pointed out. Like elements will be referenced by like reference numbers with respect to the previously described embodiment.

The mobile system 10 is mounted on a frame 26 adapted for roadability by providing wheels 120 and a hitch 122 for releasable connection to a tractor (not shown) in a conventional manner. A treated waste conveyer system 124 adapted to swing and dispense treated waste from a spout 126 allows transfer to other containers from a greater height than that provided in the stationary unit described above. A conveyer is provided in two segments 128, 130 to transport waste bags (not shown) up and over the unit into the hopper head 44 to the inlet 42 of the impactor.

The air pump 20 is mounted forwardly of the impactor in the illustrated embodiment but a location more rearward and adjacent the effluent conduit 106 is preferred. Long air conduit runs (not shown) connect the pump to the effluent conduit at the location of connection 112 atop the effluent conduit and the HEPA filters (not shown). Storage tanks 132 for NaOCL and water are provided, being strapped to the frame 26.

Figure 7:
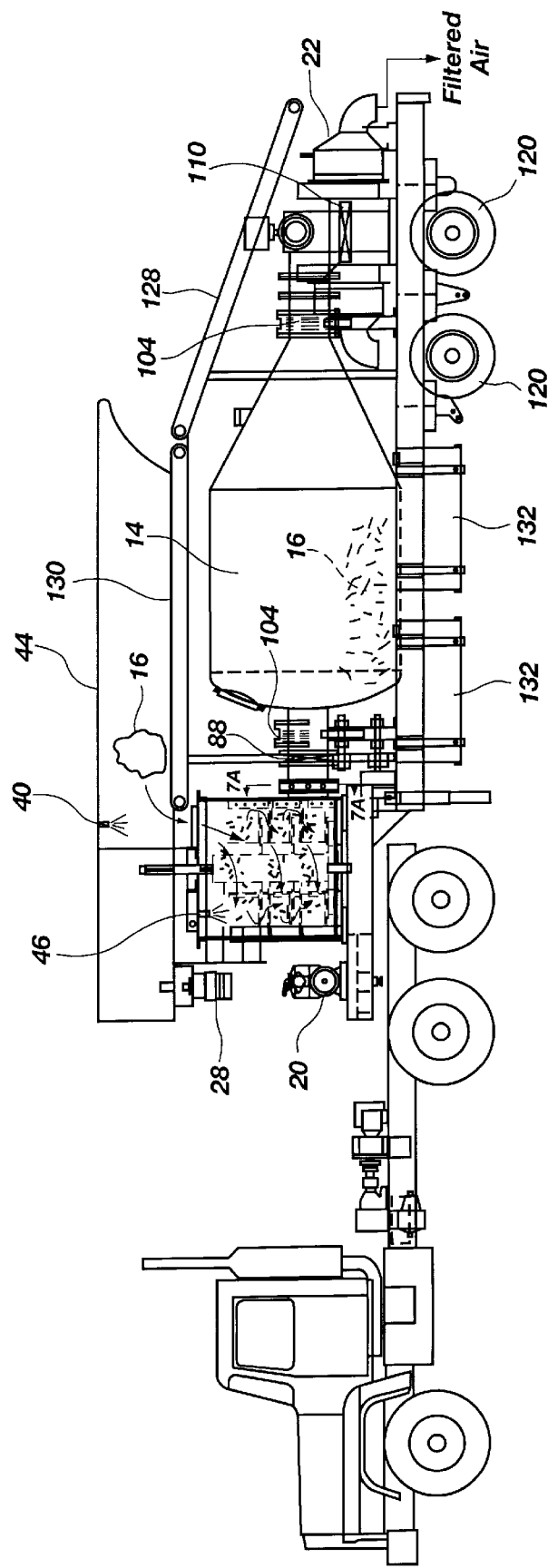
FIG. 7 of the drawings is a further side elevation view of the mobile system shown in FIG. 6, showing additional details.
Figure 8:
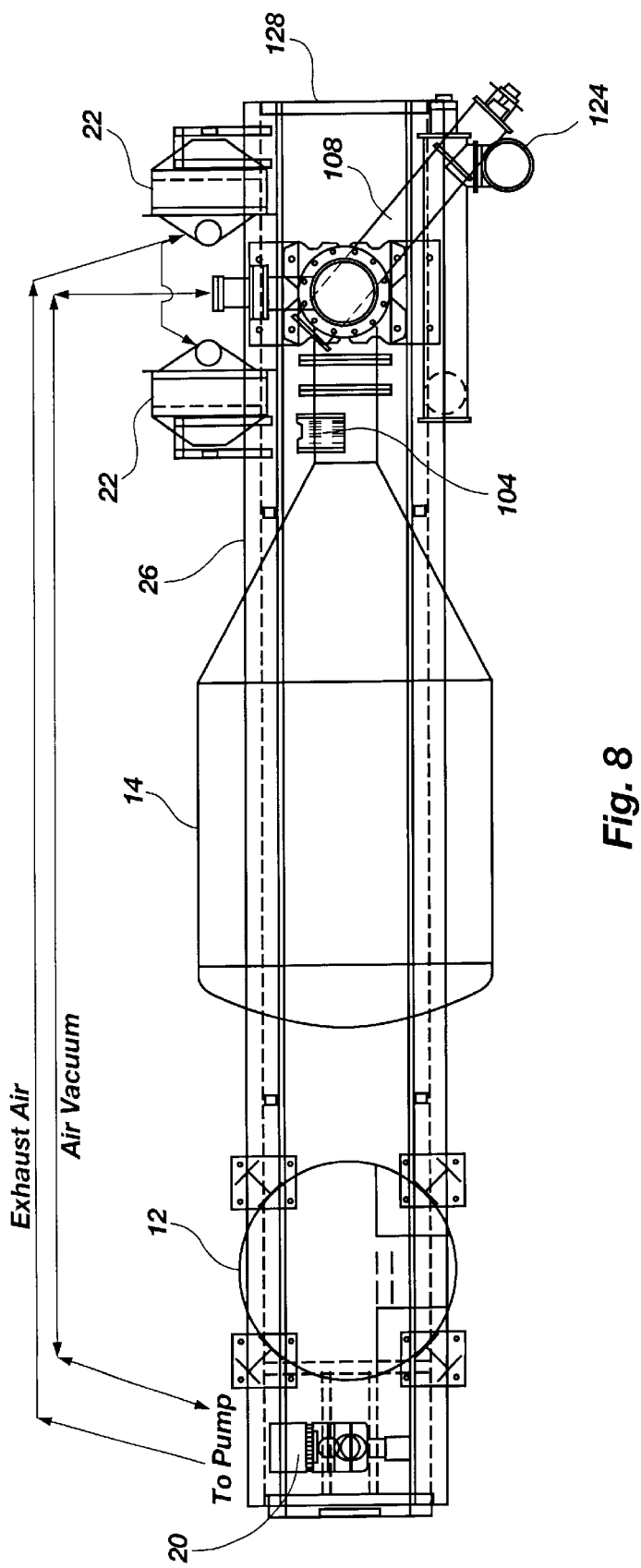
FIG. 8 is a plan view of the system shown in FIG. 7.
Figure 7A:
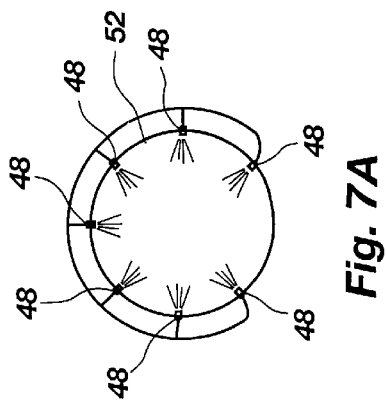
FIG. 7A is a sectional view, taken along line A—A in FIG. 7, of a portion of the system shown in FIG. 7.

Further detail can be appreciated with reference to FIGS. 7, 7A, and 8. The flow of air between the air pump 20 and effluent conduit 106 and HEPA filters 22 is illustrated schematically in FIG. 8.

As can be appreciated the system for treatment of infectious waste according to the present invention provides a simplified and economical apparatus in comparison with known systems. Advantages in costs of operation are realized by elimination of the need for treatment steps used previously and increased capacity in comparison to known systems. Further, elimination of the need for discharge of fluids into a sanitary sewer allows installation at lower cost, and in places not otherwise available due to lack of a sewer connection. Advantages in reliability is also realized as the design inherently reduces the probability of jamming, and worker safety is improved as workers do not need to clear jams. These advantages are achieved in an apparatus that is relatively less costly to construct in comparison with known systems. Accordingly, proper disposal of hazardous infectious waste is encouraged by availability of the system according to the invention, protecting human health and the environment to the extent more infectious waste is properly rendered safe for conventional disposal.

It will be apparent from the foregoing that while a particular form of the invention has been illustrated and described, various modifications can be made without departing from the spirit and scope of the invention. Accordingly, it is not intended that the scope of the invention be limited, except as by the limitations of the appended claims.

What is claimed is:

1. A system for treatment of infectious waste, comprising in combination:
   an impactor comprising a plurality of impact surfaces, adapted to pulverize the infectious waste by impact;
   an injector adapted to inject treatment fluid into the infectious waste;
   a mixer adapted to mix pulverized waste with treatment fluid;
   a pressurizable drum having an interior configured to hold pulverized waste and treatment fluid at a superatmospheric pressure; and
   an air pump adapted to apply a surcharge of air to the pressurizable drum to create a condition of superatmospheric pressure within the pressurizable drum, whereby improved absorption of treatment fluid by the pulverized waste and pathogenic organisms contained therein is enabled, and to draw air through the system, whereby airborne matter from waste fed into the impactor is drawn into the system, reducing contamination of air surrounding the system.

2. The system for treatment of infectious waste of claim 1, wherein said mixer comprises said pressurizable drum.

3. The system for treatment of infectious waste of claim 1, wherein the treatment fluid comprises Sodium Hypochlorite.

4. The system for treatment of infectious waste of claim 1, wherein the impactor further comprises:
   a housing enclosing an interior chamber, said housing defining an inlet through which infectious waste is received and an outlet through which treated waste is discharged to the mixer;
   a rotor rotatably disposed in the housing, said rotor further comprising an impact surface adapted to impart energy to solid waste constituents by impact therewith, said impact acting to break up solid waste constituents, whereby size reduction is effected; and
   a target plate comprising an impact surface carried by said housing within the interior chamber adapted to receive impacts from solid waste constituent solids whereby size reduction is effected.

5. The system for treatment of infectious waste of claim 4, wherein said mixer comprises said pressurizable drum, said pressurizable drum having a first end and a second end and being rotatable about an axis of rotation of said drum.

6. The system of claim 5, wherein said mixer further comprises said drum defining an inlet to a mixing chamber within said pressurizable drum, said inlet being located at said first end of the drum on said axis of rotation, and an outlet defined by said drum at said second end on said axis of rotation, wherethrough treated waste passes, said system further comprising:
   a first conduit connecting the outlet of the impactor to said inlet of the pressurizable drum;
   a first valve disposed in said first conduit configured to selectively seal off the pressurizable drum;
   a second conduit connected to said outlet of the pressurizable drum;
   a second valve disposed in said second conduit configured to selectively seal off the pressurizable drum, whereby said pressurizable drum is selectively pressurizable.

7. The system of claim 6, wherein said mixer further comprises spirally oriented mixing flights disposed within said mixing chamber, whereby waste and treatment fluid are mixed when the pressurizable drum is rotated in a first direction and discharged from the mixer when the pressurizable drum is rotated in a second direction.

8. The system of claim 7, wherein said system further comprises a mobile frame on which the system is carried, whereby the system is made mobile.

9. The system of claim 8, further comprising a replaceable impact element removably mounted on said rotor, said replaceable impact element comprising said impact surface of the rotor of the impactor, whereby said impact element can be replaced when it becomes excessively worn.

10. A system for treatment of infectious waste, comprising:
an impactor comprising a plurality of impact surfaces, configured to break solid waste constituents into smaller size pieces, said impactor further comprising:
a housing enclosing an interior chamber, said housing defining an inlet for receiving infectious waste and an outlet for discharging treated waste;
a rotor rotatably disposed in the housing, said rotor further comprising an impact surface adapted to impart energy to solid waste constituents by impact therewith whereby size reduction is effected;
a target plate comprising an impact surface adapted to receive impacts from solid waste constituent solids whereby size reduction is effected;
a treatment fluid injector configured to inject treatment fluid into the infectious waste treated;
a source of treatment fluid fluidly connected to the treatment fluid injector; and
an air pump configured to draw air through the impactor, whereby airborne matter from waste fed into the impactor is drawn into the system, reducing contamination of air surrounding the system.

11. The system of claim 10, further comprising:
a pressurizable mixing drum having an interior mixing chamber, configured for receiving treatment fluid and waste treated in the impactor, said pressurizable mixing drum being adapted to mix said waste and said treatment fluid;
wherein said air pump is in fluid communication with said interior mixing chamber; and
means for making the pressurizable mixing drum airtight; whereby waste and treatment fluid can be mixed at an elevated pressure.

12. The system of claim 11, wherein said rotor is oriented vertically and has a plurality of horizontal plates, each plate further comprising an impact element carried thereon, said impact element comprising said impact surface; said impactor housing further comprising a plurality of impact surfaces disposed so as to be above each horizontal plate of the rotor, and said impactor housing also comprising a shelf disposed in said interior chamber between said plurality of horizontal plates.

13. The system of claim 12, further comprising a plurality of treatment fluid injectors, wherein at least one of said injectors is configured to inject treatment fluid into said interior chamber of the impactor.

14. The system of claim 13, wherein said pressurizable mixing drum is rotatably mounted so as to rotate about an axis of rotation, the pressurizable mixing drum having an inlet at a first end of said drum and an outlet at a second end of said drum, said inlet and said outlet being aligned on said axis of rotation, and the system further comprising a conduit between the outlet of the impactor and the inlet of said drum, the system further comprising a first valve disposed between said outlet of the impactor and said inlet of the drum, the first valve opening to allow air and waste and treatment fluid to pass between the impactor and the pressurizable drum and closing to provide an air-tight seal between the impactor and said drum, and the system further comprising a second valve controlling the outlet of said drum, said second valve closing to provide an air-tight seal allowing the pressurizable mixing drum to be pressurized when said first valve is also closed and said second valve opening to allow air and treated waste mixed with treatment fluid to pass through said outlet of the pressurizable mixing drum.

15. The system of claim 14, wherein the pressurizable mixing drum further comprises spiral mixing flights configured to mix treatment fluid and waste when said drum is rotated in a first direction and move treated waste through said outlet of said drum when said drum is rotated in a second direction.

16. The system of claim 15, wherein said air pump is also configured to draw air from said drum, whereby air is drawn through said inlet of the impactor and through the impactor and through the inlet of the pressurizable mixing drum into said interior chamber thereof, whereby airborne matter from waste fed into said inlet of the impactor is drawn into the system, reducing contamination of air surrounding the system.

17. The system of claim 16, further comprising a filter fluidly connected to the air pump at an outlet thereof, said filter being adapted to filter out airborne contaminants derived from the infectious waste.

18. A system for treatment of infectious waste, comprising in combination:
a multi-stage impactor configured to break solid waste constituents into smaller size pieces, said impactor further comprising:
a housing enclosing an interior chamber, said housing defining an inlet for receiving infectious waste and an outlet for discharging treated waste;
a rotor rotatably disposed in the housing, said rotor rotating about a vertical axis and further comprising a plurality of horizontally disposed plates, each plate comprising an impact surface adapted to impart energy to solid waste constituents by impact therewith whereby size reduction is effected;
a plurality of target plates carried by said housing, each comprising an impact surface adapted to receive impacts from solid waste constituent solids whereby size reduction is effected, and each target plate being positioned above a horizontally disposed plate of said rotor; and
a plurality of horizontal shelves carried by the housing, each shelf being positioned below a horizontally disposed plate of said rotor; said shelves each defining an end to each of the stages of the impactor;
a treatment fluid injector configured to inject treatment fluid into the infectious waste treated;
a source of treatment fluid fluidly connected to the treatment fluid injector;
a pressurizable mixing drum having an interior mixing chamber, said pressurizable mixing drum receiving treatment fluid and waste treated in the impactor, said pressurizable mixing drum being adapted to mix said waste and said treatment fluid, said pressurizable mixing drum being rotatably mounted so as to rotate about an axis of rotation, the pressurizable mixing drum having an inlet at a first end of said drum and an outlet at a second end of said drum, said inlet and said outlet being aligned on said axis of rotation, and the system further comprising a conduit between the outlet of the impactor and the inlet of said drum, the system further comprising a first valve disposed between said outlet of the impactor and said inlet of the drum, the first valve opening to allow air and waste and treatment fluid to pass between the impactor and the pressurizable drum and closing to provide an air-tight seal between the impactor and said drum, and the system further comprising a second valve controlling the outlet of said drum, said second valve closing to provide an air-tight seal allowing the pressurizable mixing drum to be pressurized when said first valve is also closed and said second valve opening to allow air and treated waste mixed with treatment fluid to pass through said outlet of the pressurizable mixing drum;

an air pump fluidly connected to said interior mixing chamber of the pressurizable mixing drum whereby air is pumped into said drum to provide a superatmospheric pressure therein, said air pump also being configured to draw air from said drum, whereby air is drawn through said inlet of the impactor and through the impactor and through the inlet of the pressurizable mixing drum into said interior chamber thereof, whereby airborne matter from waste fed into said inlet of the impactor is drawn into the system, reducing contamination of air surrounding the system;

a filter fluidly connected to the air pump at an outlet thereof, said filter being adapted to filter out airborne contaminants derived from the infectious waste.

19. The system for treatment of infectious waste of claim 1, wherein said air pump is configured to draw air from said drum, whereby air is drawn through said inlet of the impactor and through the impactor and through the inlet of the pressurizable mixing drum into said interior chamber thereof, whereby airborne matter from waste fed into said inlet of the impactor is drawn into the system, reducing contamination of air surrounding the system.

20. The system for treatment of infectious waste of claim 19, further comprising a filter in fluid communication with the air pump at an outlet thereof, said filter being adapted to filter out airborne contaminants derived from the infectious waste.

21. The system for treatment of infectious waste of claim 19, wherein said mixer comprises said pressurizable drum.

* * * * *